US012648803B2

(12) United States Patent

Powers et al.

(10) Patent No.: US 12,648,803 B2

(45) Date of Patent: Jun. 9, 2026

(54) ASSEMBLY FIXTURE FOR INTRAMEDULLARY NAIL

(71) Applicant: OrthoPediatrics Corp., Warsaw, IN (US)

(72) Inventors: Chris M. Powers, Warsaw, IN (US); Michael Giordano, Osceola, IN (US); Luis Vega, Warsaw, IN (US)

(73) Assignee: OrthoPediatrics Corp., Warsaw, IN (US)

( * ) Notice: Subject to any disclaimer, the term of this patent is extended or adjusted under 35 U.S.C. 154(b) by 728 days.

(21) Appl. No.: 17/904,063

(22) PCT Filed: Feb. 10, 2021

(86) PCT No.: PCT/US2021/017432

§ 371 (c)(1),
(2) Date: Aug. 11, 2022

(87) PCT Pub. No.: WO2021/163174

PCT Pub. Date: Aug. 19, 2021

(65) Prior Publication Data

US 2023/0079526 A1 Mar. 16, 2023

Related U.S. Application Data

(60) Provisional application No. 62/972,846, filed on Feb. 11, 2020.

(51) Int. Cl.
A61B 17/90 (2006.01)
A61B 17/72 (2006.01)
(52) U.S. Cl.
CPC .............. A61B 17/90 (2021.08); A61B 17/72 (2013.01)

(58) Field of Classification Search
CPC ................................ A61B 17/90; A61B 17/72
See application file for complete search history.

(56) References Cited

U.S. PATENT DOCUMENTS 5,766,179 A 6/1998 Faccioli et al.
7,175,631 B2 2/2007 Wilson et al.
(Continued)

FOREIGN PATENT DOCUMENTS

WO 2001082804 9/2002
WO 2010037038 7/2010
WO 2014152219 9/2014

OTHER PUBLICATIONS

PCT/US2021/017432, Written Opinion of the International Searching Authority, 13 pgs, U.S. Patent and Trademark Office, Jul. 9, 2021.

Primary Examiner — Kevin T Truong
Assistant Examiner — Diana Jones
(74) Attorney, Agent, or Firm — John V. Daniluck; Gerald W. Roberts; Dentons Bingham Greenebaum LLP

(57) ABSTRACT

A system is provided for aligning an intramedullary nail for implantation when the intramedullary nail has an intramedullary nail body having a first end having a first interlocking profile and the intramedullary nail body has a first through hole extending therethrough about a first axis. The system comprises an alignment device adapted and configured to be separable from the intramedullary nail. The system also comprises a holding fixture comprising a channel and a projection adapted and configured to cooperatively receive the intramedullary nail in the channel such that the projection extends within the first through hole and the first axis aligns with a through hole of the alignment device when the first interlocking profile is engaged with an interlocking profile of the alignment device.

10 Claims, 10 Drawing Sheets

(56)     References Cited

U.S. PATENT DOCUMENTS

| | | | |
|---|---|---|---|
| 7,232,443 | B2 | 6/2007 | Zander et al. |
| 8,500,746 | B2 | 8/2013 | Fernandez |
| 8,784,430 | B2 | 7/2014 | Kay et al. |
| 9,662,153 | B2 | 5/2017 | Larsen et al. |
| 9,820,760 | B2 | 11/2017 | Purohit |
| 10,213,219 | B2 | 2/2019 | Garlock et al. |
| 11,129,628 | B2 | 9/2021 | Wieland et al. |
| 11,207,115 | B2 | 12/2021 | Schumacher et al. |
| 11,213,337 | B2 | 1/2022 | Rossney et al. |
| 11,350,951 | B2 | 6/2022 | Luo et al. |
| 2009/0266728 | A1* | 10/2009 | Turner ................. A61B 17/865 |
| | | | 206/459.1 |
| 2013/0110119 | A1 | 5/2013 | Atkinson et al. |
| 2013/0172890 | A1 | 7/2013 | Limouze et al. |
| 2014/0046380 | A1 | 2/2014 | Asfora |
| 2015/0305791 | A1 | 10/2015 | Purohit |
| 2016/0183994 | A1* | 6/2016 | Quach ................ A61B 17/8866 |
| | | | 606/90 |
| 2017/0202566 | A1* | 7/2017 | Luo .................... A61B 17/1725 |
| 2018/0116747 | A1* | 5/2018 | Matityahu .............. A61B 90/08 |
| 2023/0145104 | A1 | 5/2023 | Bauer |

* cited by examiner

1

ASSEMBLY FIXTURE FOR INTRAMEDULLARY NAIL

CROSS REFERENCE TO RELATED APPLICATIONS

This application claims the benefit of priority to U.S. Provisional Patent Application Ser. No. 62/972,846, filed Feb. 11, 2020, titled ASSEMBLY FIXTURE FOR INTRAMEDULLARY NAIL, which is incorporated herein by reference.

FIELD OF THE INVENTION

Various embodiments of the present invention pertain to apparatus and methods for the coupling together of an implantable medical device with an alignment tool.

BACKGROUND

"An intramedullary rod, also known as an intramedullary nail (IM nail) or interlocking nail or Kuntscher nail (without proximal or distal fixation), is a metal rod forced into the medullary cavity of a bone. IM nails have long been used to treat fractures of long bones of the body. Gerhard Kuntscher is credited with the first use of this device in 1939, during World War II, for soldiers with fractures of the femur. Prior to that, treatment of such fractures was limited to traction or plaster, both of which required long periods of inactivity. IM nails resulted in earlier return to activity for the soldiers, sometimes even within a span of a few weeks, since they share the load with the bone, rather than entirely supporting the bone." https://en.wikipedia.org/wiki/Intramedullary_rod (citations omitted).

Surgical alignment of intramedullary nails has been challenging.

BRIEF DESCRIPTION OF THE DRAWINGS

Some of the figures shown herein may include dimensions. Further, the figures shown herein may have been created from scaled drawings, scaled models, or from photographs that are scalable. It is understood that such dimensions, or the relative scaling within a figure, are by way of example, and not to be construed as limiting unless so stated in a claim. Persons of ordinary skill will also recognize that CAD renderings may include lines that pertain to changes in the computer model, and not necessarily to component features.

2

Figure 8:
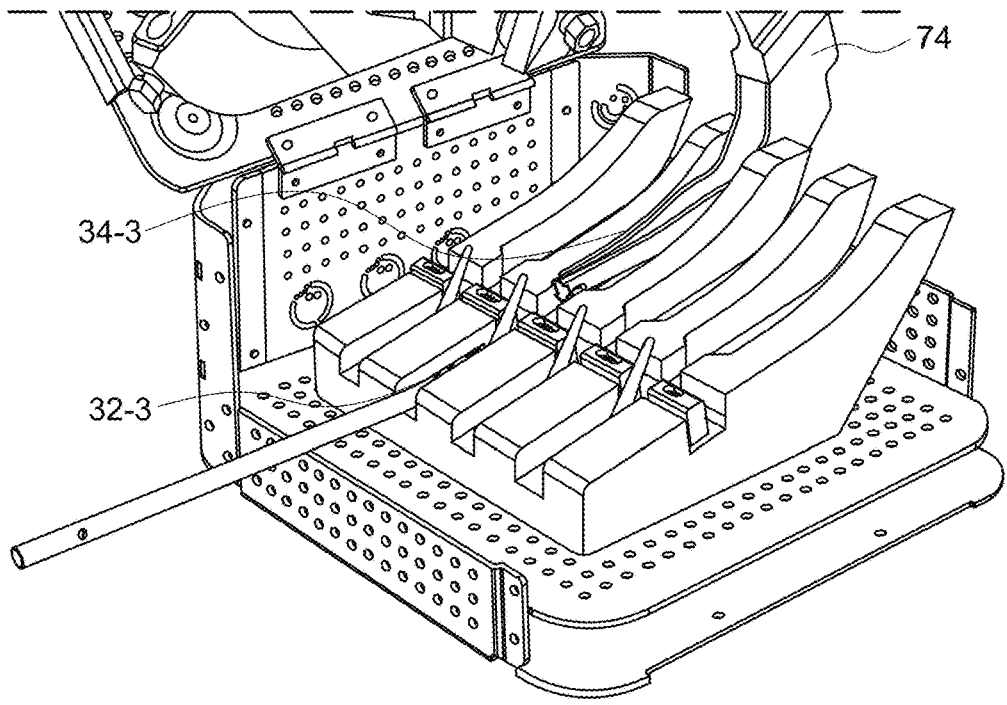
FIG. 8 is a close up of the apparatus of FIG. 7 with the implant alignment device located between walls of a channel.
Figure 9:
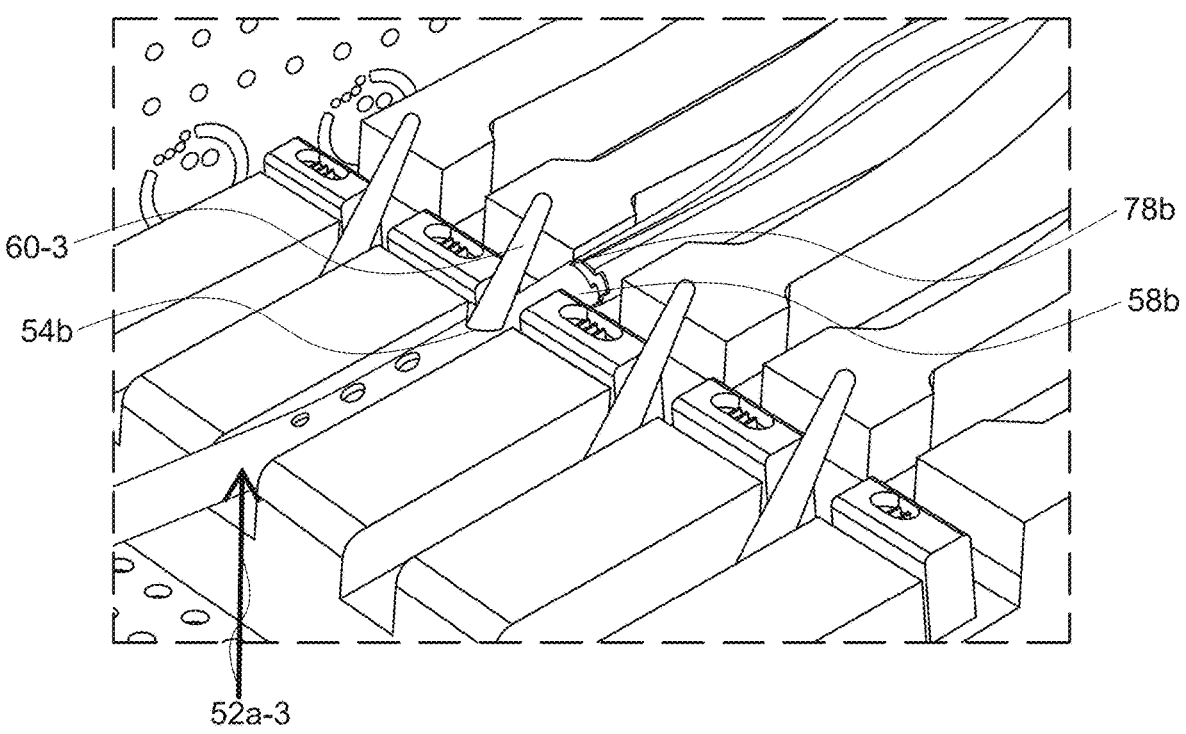

FIG. 9 is a close up of the apparatus of FIG. 8 just prior to engagement of the ends of the implant and implant alignment device.

Figure 10:
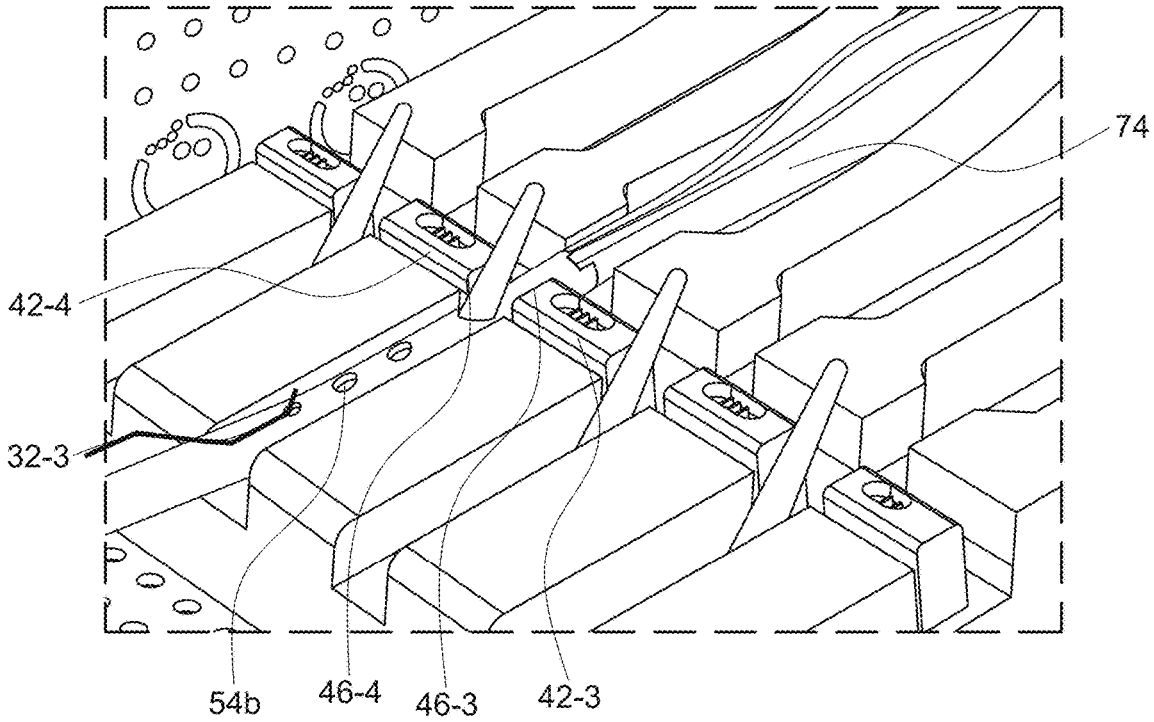

FIG. 10 shows the apparatus of FIG. 9 with the angular positioning features of the ends in full engagement.

Figure 7:
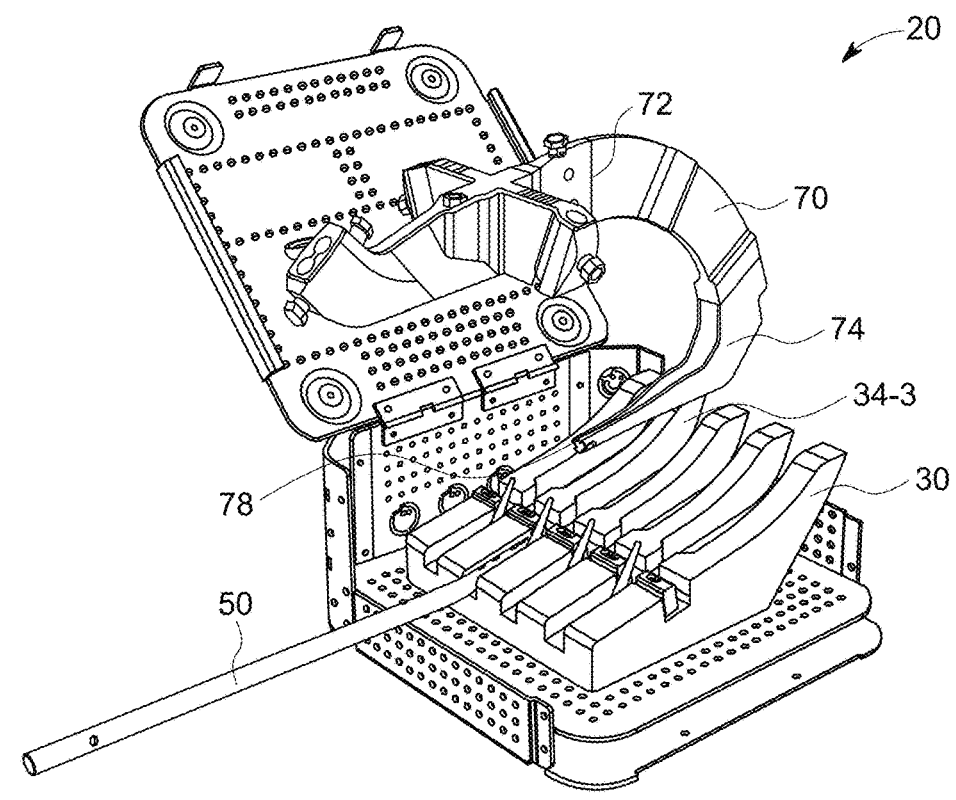
FIG. 7 is a perspective CAD rendering of a kit according to one embodiment of the present invention.
Figure 11:
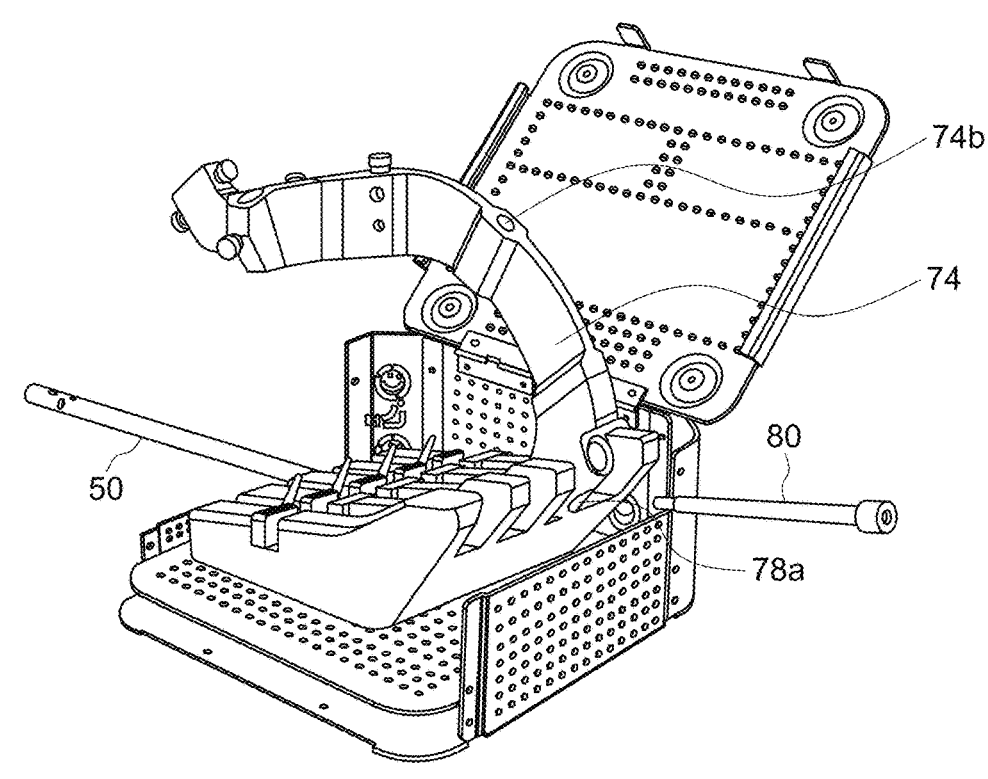

FIG. 11 shows the apparatus of FIG. 7 from the opposite side, with a fastener aligned for insertion through the end fastener hole of the alignment device.

Figure 12:
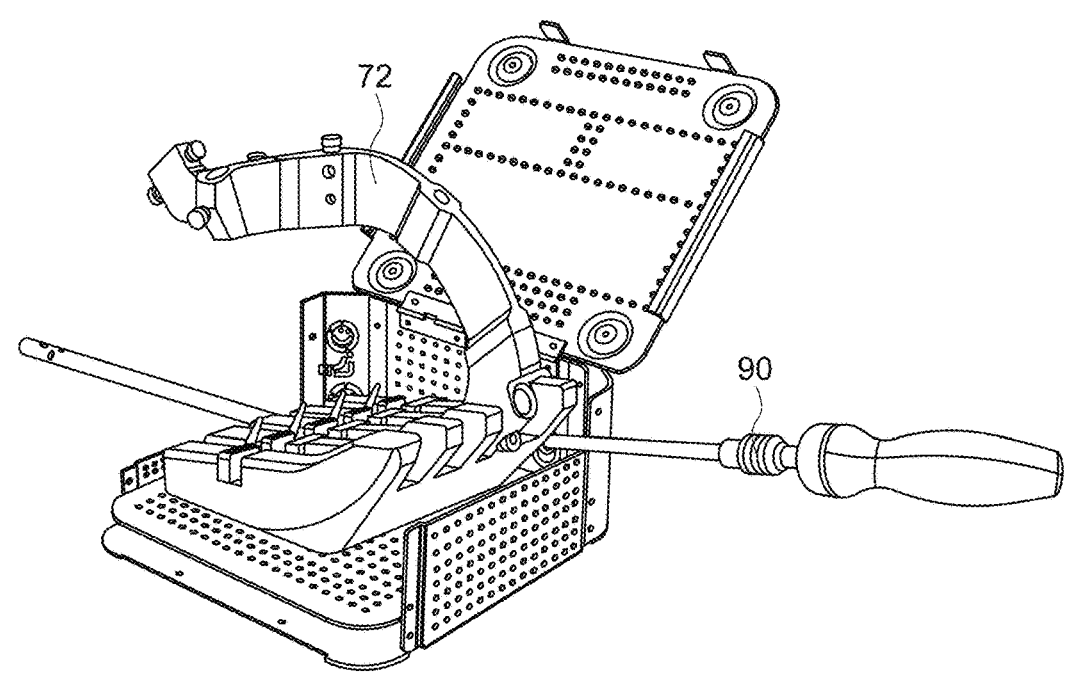

FIG. 12 shows the apparatus of FIG. 11 with a tool being aligned with the fastener for coupling of the implant with the implant alignment device.

Figure 13:
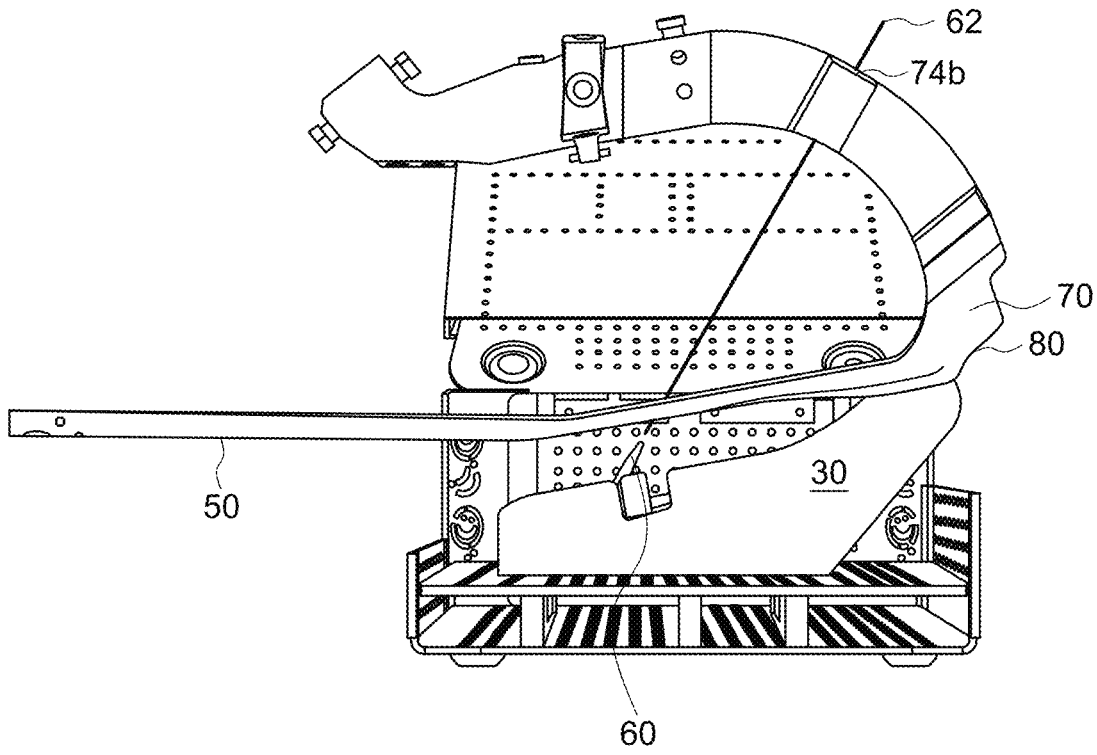

FIG. 13 shows the coupled assembly of the implant and the implant alignment device being removed from the alignment fixture.

Figure 14:
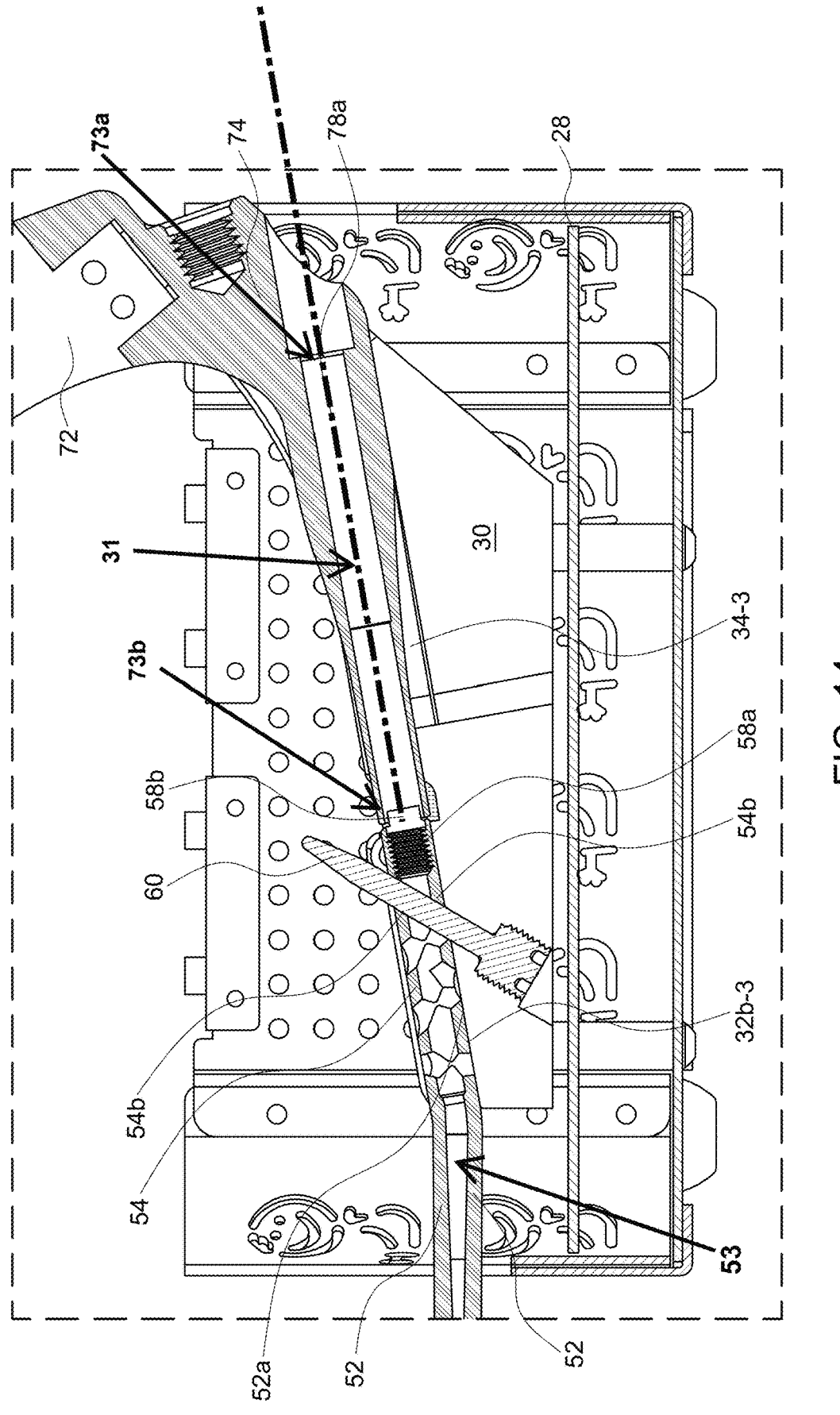

FIG. 14 is a side elevational cross sectional CAD rendering of the apparatus of FIG. 11, looking from the front toward the rear.

ELEMENT NUMBERING

The following is a list of element numbers used with all of the embodiments, and at least one noun used to describe that element. In some instances, an "X" or other letter and/or an additional number (0 or greater) may be appended to one or more of these element numbers in the text and/or drawings. Consistent with the corresponding description, such appended element numbers identify elements that may be used among multiple embodiments, and aspects of a particular such element stated for one embodiment can be applied to the corresponding element in a different embodiment, except as shown and described differently, and as would be understood by a person of ordinary skill in the art. It is understood that none of the embodiments disclosed herein are limited to these nouns, and these element numbers can further include other words that would be understood by a person of ordinary skill reading and reviewing this disclosure in its entirety.

| | |
|---|---|
| 10 | kit |
| 20 | container |
| 21 | handle |
| 22 | lid |
| 24 | sides |
| 26 | bottom |
| 28 | platform |
| 30 | holding fixture |
| 31 | channel |
| 32 | first channel |
| a | first width |
| b | contact surface |
| 34 | second channel |
| a | second width |
| 38 | cross channel |
| 40 | retention mechanism; means for retaining the nail within the channel; lateral locating feature |
| 42 | body |
| 43 | axial registration feature |
| 44 | spring |
| 46 | bearing |
| 50 | intramedullary nail |
| 51 | nail body |
| 52 | first section |
| a | contact surface |
| 53 | through hole |
| 54 | second section |
| b | lateral bone fastener holes |
| c | alignment axis |
| 58 | end |
| a | threaded hole |
| b | angular positioning and interlocking feature |

-continued

| 60 | alignment pin or projection; |
| | means for registering the nail |
| | along the channel; axial |
| | registration feature |
| 62 | alignment axis |
| 70 | implant alignment device |
| 72 | handle |
| 73 | through hole |
| a | third though hole |
| b | fourth through hole |
| 74 | body |
| b | lateral fastener tooling hole |
| 78 | end |
| a | end bone fastener hole |
| b | angular positioning and interlocking feature |
| 80 | Fastener shank |
| 90 | tightening tool |

DETAILED DESCRIPTION OF ONE OR MORE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention, and further permits the reasonable and logical inference of still other embodiments as would be understood by persons of ordinary skill in the art.

It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "various embodiments" or "preferably," refers to features and aspects that are present in at least one embodiment, but which are optional for some embodiments, it therefore being understood that use of the word "preferably" implies the term "optional."

Various embodiments described herein provide a system for aligning an intramedullary nail for implantation. The system comprises an intramedullary nail having a body with a first end. The first end has a first interlocking profile. The body has a first through hole extending through the body about a first axis. The system also comprises a separable alignment device with a second end having a second interlocking profile that is adapted and configured to establish a predetermined angular orientation between the alignment device and the nail when the first profile and the second profile are engaged with each other. The alignment device has a second through hole. The system also comprises a holding fixture having at least one channel and a projection. The nail is receivable in the channel with the projection extending within the first through hole. The first axis aligns with the second through hole when the first profile is engaged with the second profile.

Various embodiments described herein provide another system for aligning an intramedullary nail for implantation. The system comprises an intramedullary nail having a body with a first end. The body has a first through hole extending through the body about a first axis, and a second threaded hole in the first end. The system also comprises a fastener having a shank threadably engageable with the second threaded hole. The system also comprises a separable alignment device having a third through hole and a fourth through hole. The fourth through hole is adapted and configured to receive therethrough the shank of the fastener. The system also comprises a holding fixture having at least one channel and a means for retaining the body within the channel. The retention of the body within the channel and alignment of the third through hole with first axis further aligns the second threaded hole with the fourth through hole and permits placement of the fastener through the fourth through hole and into threaded engagement with the second threaded hole for attachment of the nail to the alignment device.

Various embodiments described herein provide another system for aligning an intramedullary nail for implantation. The system comprises an intramedullary nail having a body with a first end. The first end has a first interlocking profile. The body has a registration feature, and a second threaded hole in the first end. The system also comprises a fastener having a shank threadably engageable with the second threaded hole. The system also comprises a separable alignment device with a second end having a second interlocking profile that is adapted and configured to establish a predetermined angular orientation between the alignment device and the nail when the first profile and the second profile are engaged with each other. The device alignment device has a fourth through hole. The fourth through hole is adapted and configured to receive therethrough the shank of the fastener. The system also comprises a holding fixture having at least one channel having a channel axis and a means for locating the body along the channel axis. The locating means and the registration feature cooperate to fix the location of the body along the channel axis. The engagement of the first profile of the fixed body with the second profile aligns the second threaded hole with the fourth through hole and permits placement of the fastener through the fourth through hole and into threaded engagement with the second threaded hole.

FIGS. 1-14 show various aspects of apparatus and methods for pre-surgical alignment of an implant with an implant alignment device. Preferably, these embodiments pertain to an implant that includes at least one feature (such as a hole for a fastener) that, after implantation, will be located within a bone, and which will be fastened or otherwise joined to an external surface of the bone. In some embodiments, the implant alignment device has means for aligning that one feature of the implant relative to a second feature (such as a drill guide) of the alignment device. When the alignment device and the implant are coupled together, the implant bone hole and the alignment device drill guide are established to be coaxial.

While the alignment device and the implant are in a holding fixture, a fastener is used and the device and the implant are preferably rigidly fastened together. This assembly is then manipulated by the surgeon such that at least a portion of the implant is placed within an internal cavity of the bone, and portions of the device remain external to the bone. The alignment device preferably includes means for locating a tool (such as the bit of a drill), such that the drill bit will penetrate into the patient, through the bone, and align with the internal feature of the implant. The alignment device is then removed from the implant, leaving the implant in place in its proper location in the bone by attachment of the external fastener.

Figure 1:
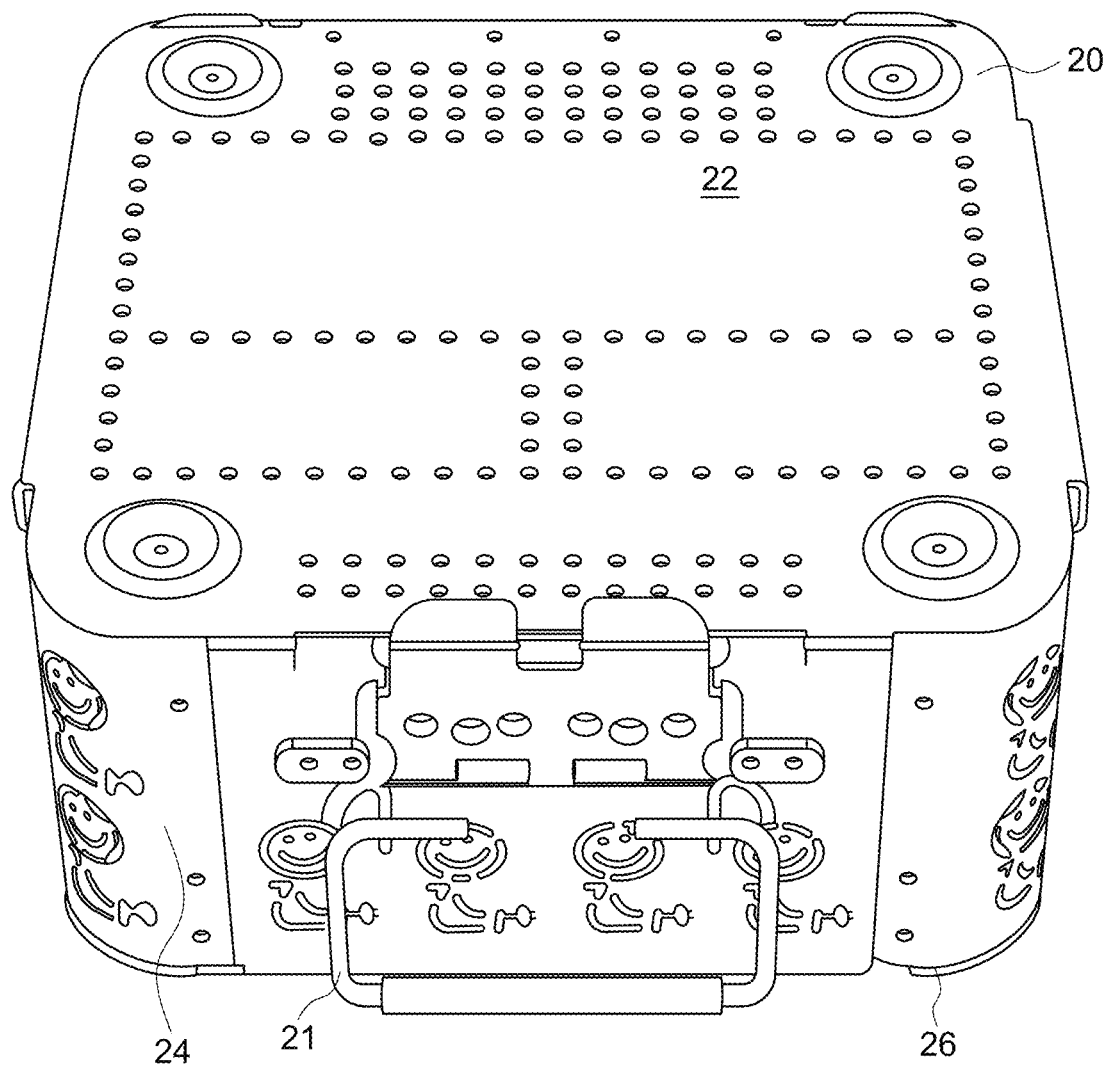
FIG. 1 is a CAD rendering of a sterilizable container for an alignment fixture according to one embodiment of the present invention.

FIG. 1 shows a container 20 that provides a platform for establishing a connection between hardware adapted and configured to be implantable within a patient and an alignment device adapted and configured to provide a predetermined fixed orientation between the hardware and the device. Preferably, the container 20 is adapted and configured to be readily sterilized, such as with the use of a plurality of through holes in the sides 24 and bottom 26. Container 20 includes a handle to facilitate carrying and storage.

Figure 2:
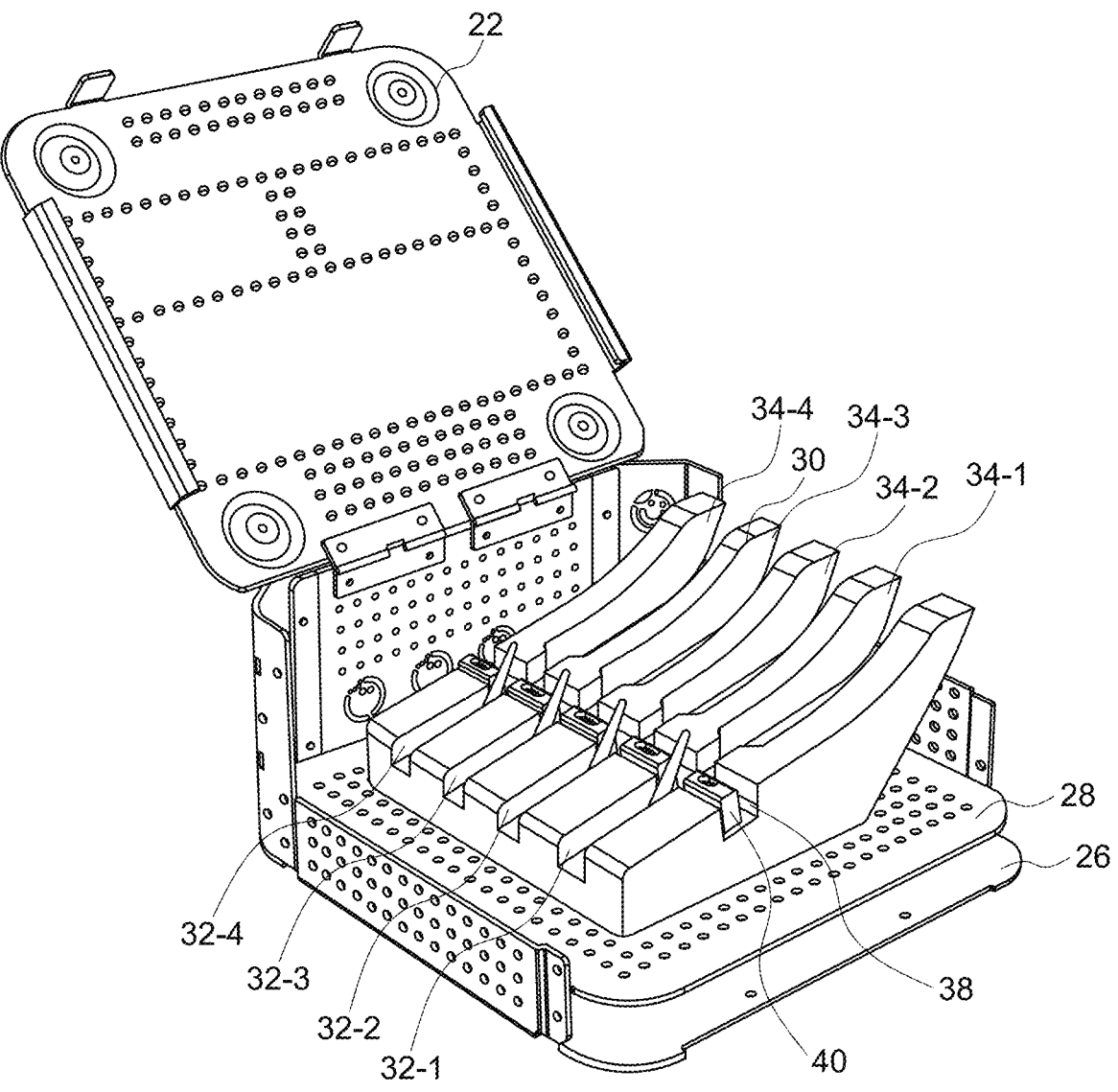
FIG. 2 is a perspective CAD rendering of the apparatus of FIG. 1, with the lid opened and some of the sides removed.

FIG. 2 shows container 20 with the lid 22 opened, and one or more of the sides 24 removed. A platform 28 within container 20 preferably supports a holding fixture 30. Fixture 30 includes at least one channel 32 adapted and configured to support the implantable hardware. However, in yet other embodiments, fixture 30 includes a second channel 34 aligned with the first channel 32, the second channel 34 providing temporary support of an alignment device 70.

Figure 3:
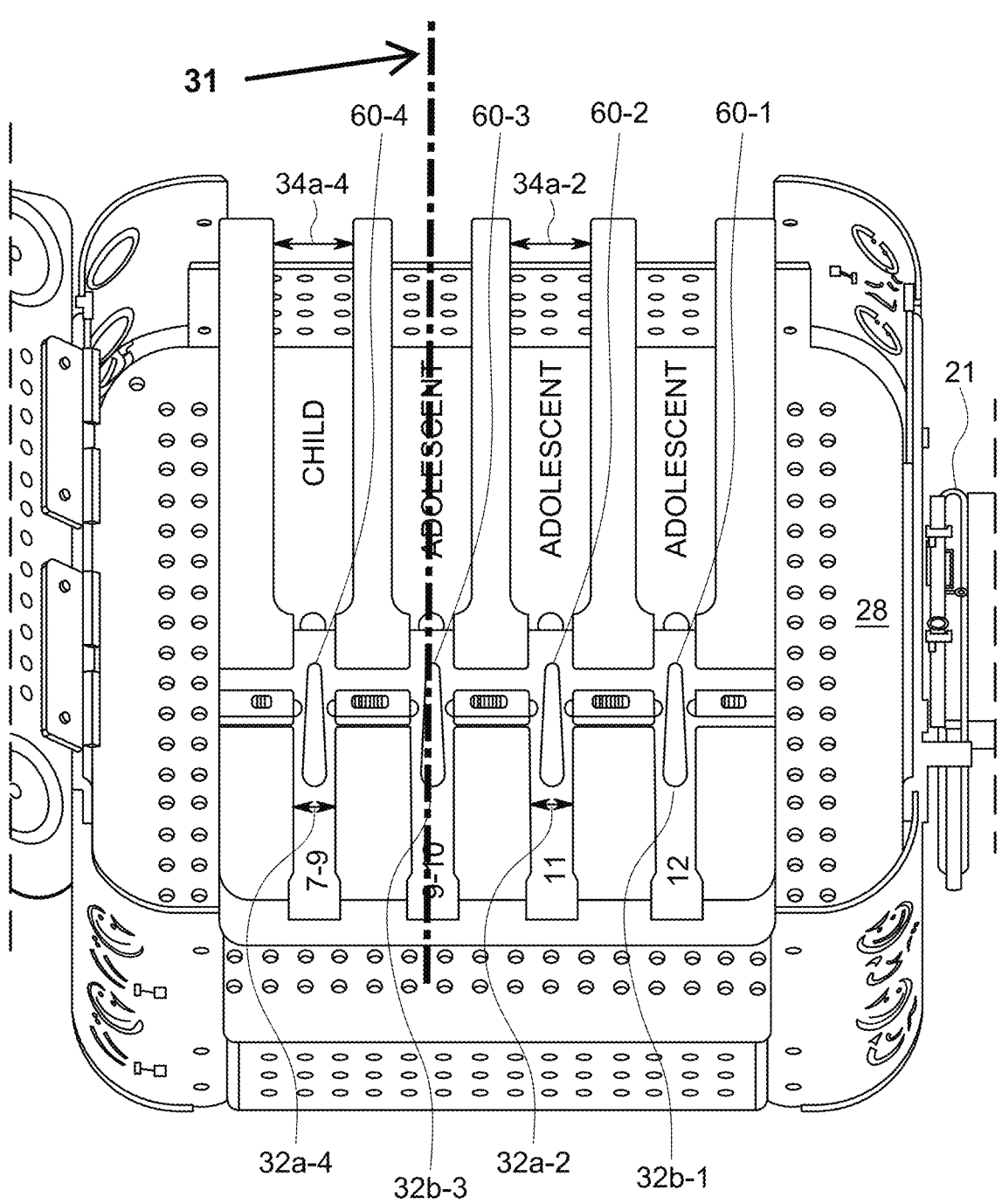
FIG. 3 is a top view looking downward of a perspective CAD rendering of the apparatus of FIG. 2.
Figure 4:
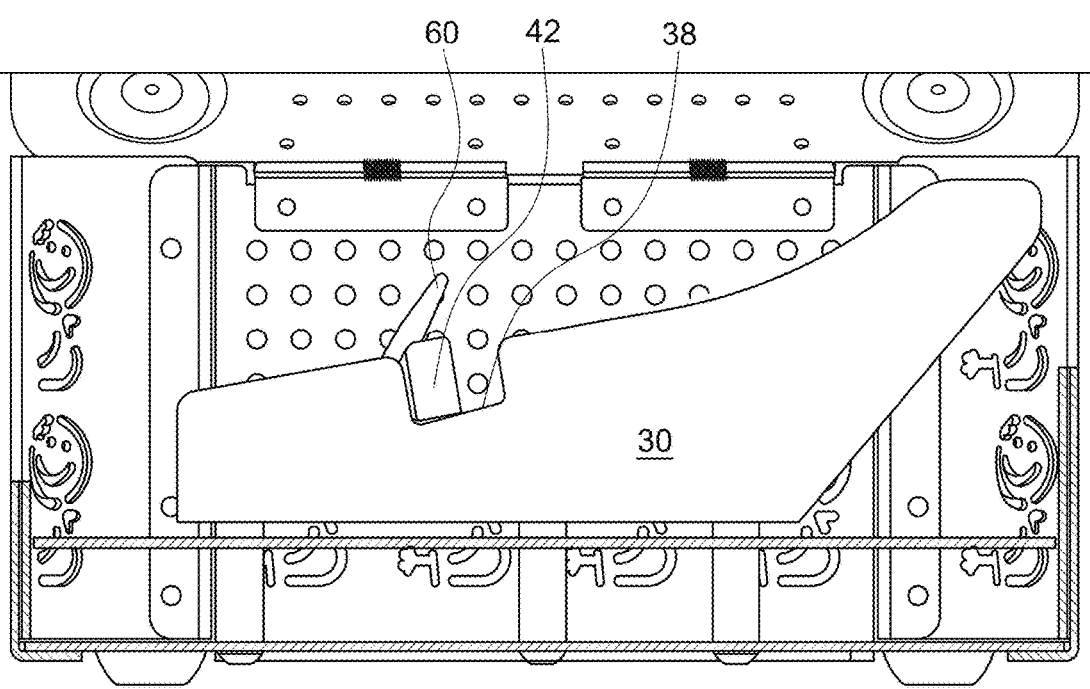
FIG. 4 is a side elevational CAD rendering of the device of FIG. 2, looking from the front to the rear.

In some embodiments, fixture 30 includes a plurality of first channels 32-1, 32-2, 32-3, and 32-4, each of them being aligned with a corresponding second channel 34-1, 34-2, 34-3, and 34-4. As best seen in FIG. 3, the channel 32 is configured to locate within it different sizes of implants. As one example, channel 32-4 has a width 34a-4 that is sized to contain within it an intramedullary nail adapted and configured to fit within a long bone of a child. It can further be seen that in those embodiments having multiple channels, the other channels can be adapted and configured to locate within them implants of different sizes. It can be seen that the width 32a-2 of channel 32-2 is larger than the width of channel 32-3, and smaller than the width of channel 32-1. However, in some embodiments, the second channels 34 are adapted and configured to locate within them the same alignment device. It can be seen that the second channels 34-4 and 34-2 have corresponding widths 34a-4 and 34a-2 that are the same.

Figure 5:
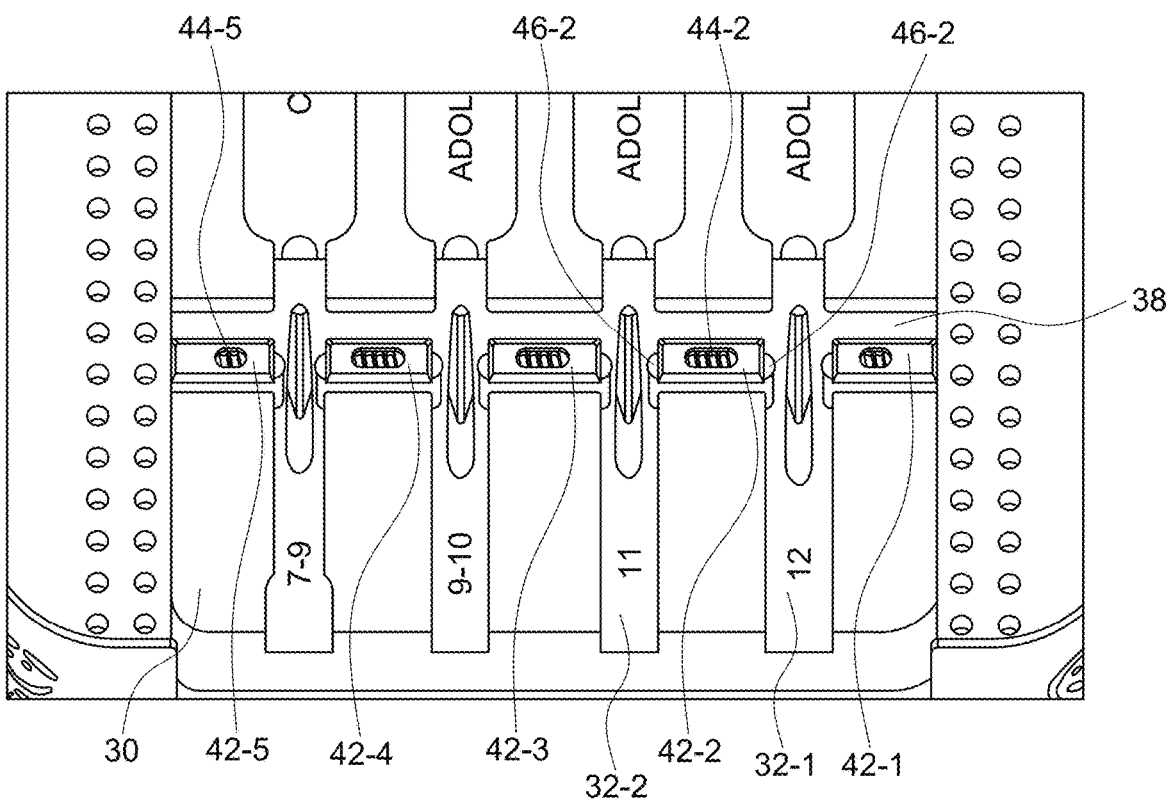
FIG. 5 is a close up of the apparatus of FIG. 3.

FIGS. 2, 3, and 5 further show a retention mechanism 40 that provides means for retaining the implant within the first channel. Retention mechanism 40 is located in a cross channel 38 that preferably is located between the first channel and the second channel. In some embodiments, the means for retaining the implant includes an alignment feature 60, such as a pin, projection, or any kind of feature that will register with a corresponding feature on the implant.

In some embodiments, retention mechanism 40 is adapted and configured to secure an implant within a first channel. In some embodiments means 40 includes a body 42 that contains within it a spring 44 that applies a biasing force on a captured bearing 46. Referring to FIG. 5, it can be seen that a body 42-2 located between first channels 32-1 and 32-2 includes within it a spring 44-2 located centrally within the body.

On either lateral side of body 42-2 is a loose but captured cylindrical or spherical bearing 46-2. Each of these bearings 46 have a diameter that is greater than a corresponding side slot (not shown) within body 42, such that the loose bearings 46 are free to move within the interior of body 42, but cannot exit the interior of the body. The central spring 44 urges each bearing 46 outwardly. Referring to FIG. 5, it can be seen that one bearing 46-2 extends into channel 32-1, and the other bearing 46-2 extends into the channel 32-2.

Although what has been shown and described is a retention mechanism 40 that includes a pair of spring-loaded bearings to push an implant generally toward the center of a channel, it is understood that the invention is not so limited and contemplates any means for retaining the implant within the channel. As another example, retention means 40 could include a single spring-loaded bearing that pushes the implant toward one wall of the channel. Still further, retention means 40 can include mechanisms that contact the top of the implant, and push the implant toward the bottom of the channel, such that the implant is retained by friction. Such other embodiments include a hinged, clamp that is manually applied to the implant after it is placed in the channel. In still further applications, the channel can include a top surface (such as a channel that includes a hole) that prevents the implant from tilting out of the channel prior to attachment of the implant to the alignment device. In still further embodiments, the channel can be fabricated from a plastic material that has a channel shaped to be close-coupled to the outer surface of the implant, such that the implant snaps into the channel and is retained by friction.

Referring briefly to FIG. 10, it can be seen that an implant 50 such as an intramedullary nail is located within channel 32-3. A bearing 46-3 pushes against one side of nail 50, and another bearing 46-4 presses against the opposite side of channel 32-3. As a result, the implant 50 is laterally restrained within channel 32-3, such that there is little or no lateral looseness, which would otherwise interfere with alignment of the implant 50 with the alignment device 70, which will be explained later.

Figure 6:
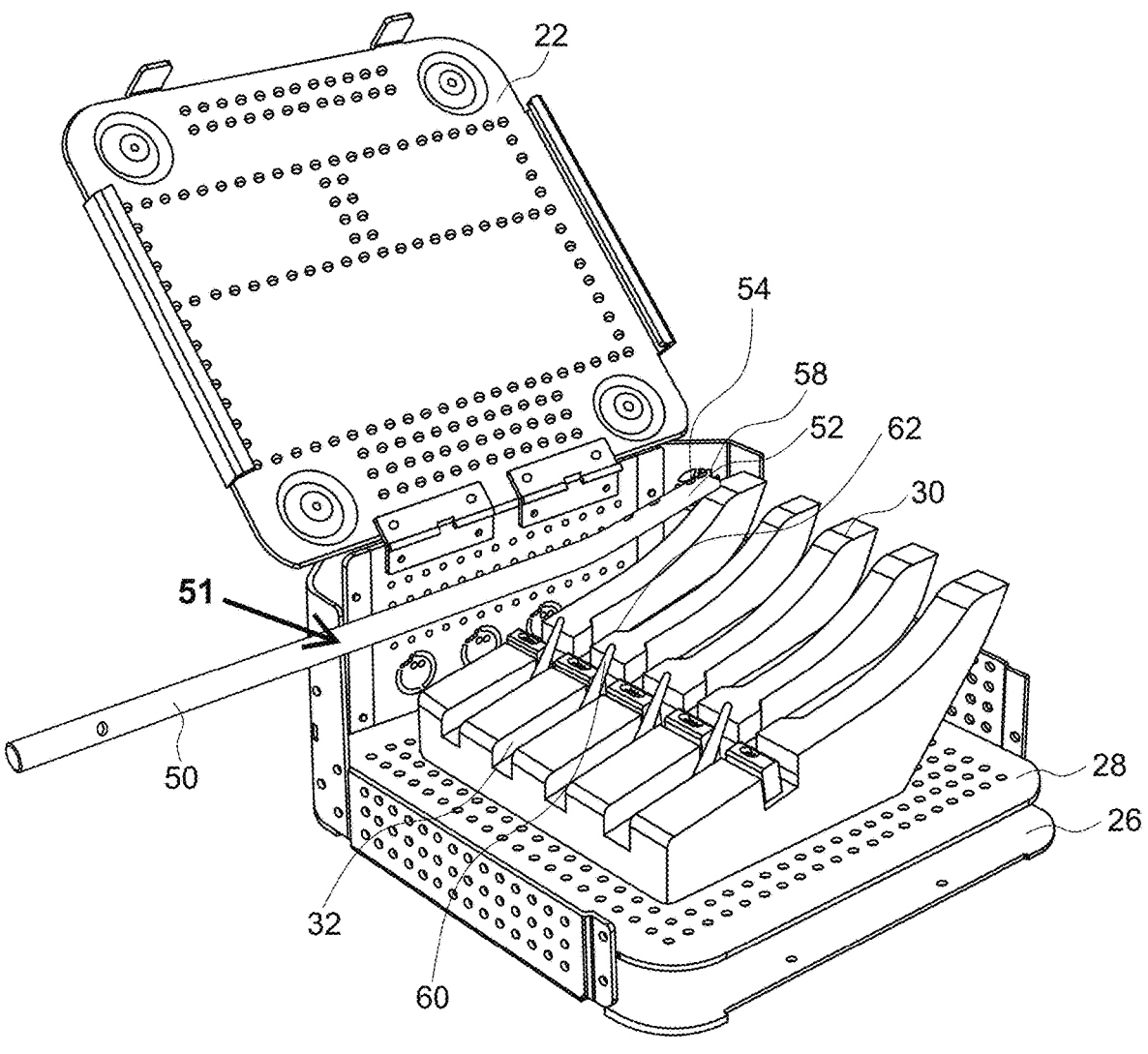
FIG. 6 shows the apparatus of FIG. 2 and including an implantable medical device prior to insertion into the fixture.

Referring to FIGS. 3 and 6, in some embodiments each of the first channels 32 preferably include a corresponding alignment pin 60. Each of the first channels 32-X include a corresponding alignment pin 60-X. In some embodiments, these alignment pins are oriented relative to the channel so as to place the corresponding implant within a predetermined angular orientation and at a predetermined axial location. However, yet other embodiments of the present invention contemplate means for registering the implant in the channel that locate the implant at only a longitudinal position along the length of the channel, or only laterally to a position within the width of the channel.

Some embodiments of the present invention pertain to apparatus and methods for retaining and aligning intramedullary nails. FIG. 6 is an exploded, perspective view of the apparatus of FIG. 2, showing an intramedullary nail prior to placement within a channel. The nail includes a plurality of through holes used for attachment of the nail 50 to a bone by way of a fastener. FIG. 6 shows nail 50 with a corresponding through hole 54 located along an alignment axis 62 that extends from a projection 60.

FIG. 7 shows the nail 50 placed within a channel 32-3 such that the bottom surface 52a of the nail 50 is placed in contact with contact surface 32b-3 of the channel, as best seen in FIG. 14. FIG. 14 further shows the projection 60 extending through a pair of through holes 54b located in the second section 54 on opposite sides of nail 50.

Referring again to FIG. 7, an implant alignment device 70 is shown located above a corresponding second channel 34-3 of fixture 30. Alignment device 70 includes a handle 72, which includes at least one tooling hole 74b (as seen in FIG. 13) that will later be used for the accurate placement of one or more other tools (not shown) that will be used to locate a bone fastener (not shown) externally to the patient's bone, and further extending within hole 54b of implant 50.

Alignment device 70 further includes a body 74 having an end 78 that is adapted and configured for alignment with the end 58 of implant 50.

FIG. 8 shows that as the user lowers alignment device 70 within the channel 34-3, that the side walls of the channel provide approximate lateral location for the end 78. FIG. 9 shows that as the alignment device 70 is fully located within channel 34-3 (as also shown in FIG. 14), that the angular positioning feature 78*b* of end 78 comes into approximate alignment with the end interlockinq feature 58*b* of implant 50. Note that the position of implant 50 is relatively fixed within channel 32-3, such that pin 60-3 and hole 54*b* coact to provide a fixed axial position within the channel, and further that the retention bodies 42 on either side of the channel provide approximate lateral placement, and generally remove any looseness of the implant within the channel. FIG. 10 shows body 74 moved longitudinally within channel 34-3, and with that the angular positioning and interlocking features 58*b* and 78*b* in face-to-face contact, whereas FIG. 9 shows these two features separated.

FIGS. 11 and 12 depict the subsequent assembly and attachment of tool 70 and implant 50. A fastening screw 80 is aligned within a through hole 78*a* (as best seen in FIG. 14) that extends from an opened end of the tool to a threaded portion [[58*a*]] within the end 58*a* of implant 50, as best seen in FIG. 14. FIG. 12 depicts the next action taken by the user, which is to use a tool 90 to threadably engage fastener 80 so as to rigidly couple alignment device 70 and implant 50 by threaded connection to the threaded connection 58*a*. FIG. 13 shows the completed assembly being removed from fixture 30, with the lateral tooling hole 74*b* being properly aligned along axis 62 with the corresponding hole 54*b* of implant 50. The completed assembly can now be used by the surgeon to introduce the intramedullary nail 50 within the intramedullary cavity of a long bone.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A system for aligning an intramedullary nail prior to implantation when the intramedullary nail has an intramedullary nail body having a first end having a first interlocking profile and the intramedullary nail body has a first through hole extending therethrough about a first axis, the system comprising:

an alignment device adapted and configured to be separable from the intramedullary nail, the alignment device comprising a second through hole and a second end, the second end comprising a second interlocking profile adapted and configured to establish a predetermined angular orientation between the alignment device and the intramedullary nail when the first interlocking profile and the second interlocking profile are engaged with each other; and a holding fixture comprising a channel and a projection located within the channel, being configured to cooperatively receive the intramedullary nail in the channel such that the projection extends within the first through hole and the first axis aligns with the second through hole when the first interlocking profile is engaged with the second interlocking profile.

2. The system of claim 1 wherein said holding fixture includes a bearing adapted and configured to retain the intramedullary nail within the channel.

3. The system of claim 1 wherein said holding fixture includes a plurality of channels, the plurality of channels being adapted and configured to locate within them intramedullary nails of different sizes.

4. A system for preparing an intramedullary nail implant prior to implantation, the system comprising:

an intramedullary nail having a body with a first end, the first end having a first interlocking profile, the body having a first through hole extending through the body about a first axis;

an alignment device being separable from the intramedullary nail, the alignment device having a second end having a second interlocking profile that is configured to establish a predetermined angular orientation between the alignment device and the intramedullary nail when the first interlocking profile and the second interlocking profile are engaged with each other, the alignment device having a second through hole; and a holding fixture having at least one channel and a spring-loaded bearing located adjacent the channel, wherein the intramedullary nail is receivable in the channel with the spring-loaded bearing being configured to resist removal of the nail from the channel.

5. The apparatus of claim 2 which further comprises a projection located within the channel, and the projection extends within the first hole when the intramedullary nail is received within the channel.

6. A method for intramedullary nail alignment prior to implantation, the method comprising:

providing an intramedullary nail having a first end having a first interlocking profile and having a first through hole extending through the intramedullary nail body about a first axis;

providing an alignment device adapted and configured to be separable from the intramedullary nail, the alignment device comprising a second through hole and a second end, the second end comprising a second interlocking profile adapted and configured to establish a predetermined angular orientation between the alignment device and the intramedullary nail when the first interlocking profile and the second interlocking profile are engaged with each other;

providing a holding fixture comprising a channel and a projection adapted and configured to cooperatively receive the intramedullary nail in the channel such that the projection extends within the first through hole and the first axis aligns with the second through hole when the first interlocking profile is engaged with the second interlocking profile;

positioning the intramedullary nail in the channel;

extending the projection within the first through hole concurrently with said positioning the intramedullary nail;

aligning the first axis with the second through hole concurrently with sad extending the projection; and engaging the first interlocking profile with the second interlocking profile after said aligning the first axis.

7. The method of claim 6 which further comprises retaining the intramedullary nail within the channel of the holding fixture with a spring loaded bearing.

8. A system for aligning an intramedullary nail prior to implantation, the system comprising:

a plurality of intramedullary nails each having a body, with one said intramedullary nail having a width different than the width of another of said plurality of intramedullary nails, and with a first end, the body of the intramedullary nail having a first through hole extending through the body of the intramedullary nail about a first axis, and the body of the intramedullary nail having a second threaded hole in the first end;

a fastener having a shank threadably engageable with the second threaded hole;

an alignment device being separable from the intramedullary nail and having a third through hole and a fourth through hole, the fourth through hole being adapted and configured to receive therethrough the shank of the fastener; and a holding fixture having a plurality of channels with one of said channels configured to receive therein said one intramedullary nail and another of said channels configured to receive therein said other intramedullary nail, wherein retention of the body of the intramedullary nail within the one of the channels and alignment of the third through hole with first axis further aligns the second threaded hole with the fourth through hole and permits placement of the fastener through the fourth through hole and into threaded engagement with the second threaded hole for attachment of the nail to the alignment device.

9. The system of claim 8 wherein said plurality of channels each have a corresponding width, the width of one of said plurality of channels being different than the width of another of said plurality of channels.

10. The system of claim 8 wherein said holding fixture includes a spring loaded bearing for retaining said intramedullary nail within the channel.

\* \* \* \* \*